(12) United States Patent
Choi et al.

(10) Patent No.: US 6,743,898 B2
(45) Date of Patent: Jun. 1, 2004

(54) MONOCLONAL ANTIBODIES THAT SUPPRESS B CELL GROWTH AND/OR DIFFERENTIATION

(75) Inventors: Yong Sung Choi, New Orleans, LA (US); Li Li, New Orleans, LA (US)

(73) Assignee: Ochsner Clinic Foundation, New Orleans, LA (US)

( * ) Notice: Subject to any disclaimer, the term of this patent is extended or adjusted under 35 U.S.C. 154(b) by 1 day.

(21) Appl. No.: 09/808,847

(22) Filed: Mar. 15, 2001

(65) Prior Publication Data

US 2003/0165508 A1 Sep. 4, 2003

(51) Int. Cl.$^7$ ................................................ C12P 21/08
(52) U.S. Cl. ............................ 530/388.73; 530/387.9; 530/388.8; 530/387.3; 435/343.1; 435/344; 435/346
(58) Field of Search ................... 530/388.73, 387.9, 530/388.8, 387.3; 435/343.1, 344, 346

(56) References Cited

PUBLICATIONS

Choi YS, et al. Immunol Res 1997; 16 (2): 161–174.*
Li L, et al. Tissue Antigens 2000; 55 (Suppl. 1): 26 (Abstract D.22).*
Li L et al. J Exp Med 2000 Mar. 20; 191 (6): 1077–1083.*
Choe J, et al. J Immunol 2000; 164: 56–63.*
Jung J, et al. Eur J Immunol 2000; 30: 2437–2443.*
Zhang X, et al. J Immunol 2001; 167: 49–56.*
Database BIOSIS, Accession No. 2001:258380; Zhang X, et al. FASEB J Mar. 8, 2001; 15 (5): A1044.*
Database BIOSIS, Accession No. 2002:369154; Zhang X, et al. FASEB J Mar. 20, 2002; 16 (4): A721.*
Database GENBANK, Accession No. AF161254; Li L, et al. Apr. 4, 2000 (direct submission).*
Rasmussen AM, et al. J Immunol Methods Feb. 5, 1992; 146 (2): 195–202.*
Kohler G, et al. Biotechnology; 24: 524–526.*
Rudikoff S, et al. Proc Natl Acad Sci USA Mar. 1982; 79: 1979–1983.*
Stancovski I, et al. Proc Natl Acad Sci USA 1991; 88: 8691–8695.*
Gura T. Science 1997; 278: 1041–1042.*
Vitetta ES, et al. Cancer Res 1994; 54: 5301–5309.*
Bodey B, et al. Anticancer Res 2000; 20: 2665–2676.*
Bowie JU, et al. Science 1990; 247: 1306–1310.*
Bergers G, et al. Cur Opin Genet Develop 2000; 10: 120–127.*

* cited by examiner

Primary Examiner—Anthony C. Caputa
Assistant Examiner—Stephen L. Rawlings
(74) Attorney, Agent, or Firm—Scully, Scott, Murphy & Presser

(57) ABSTRACT

The present invention provides monoclonal antibodies which interfere with the interactions between FDCs and B cells, thereby suppressing the proliferation and/or differentiation of B cells in lymphoid follicles. The monoclonal antibodies of the present invention are useful for treating follicular lymphomas, multiple myeloma as well as autoimmune diseases.

7 Claims, 11 Drawing Sheets

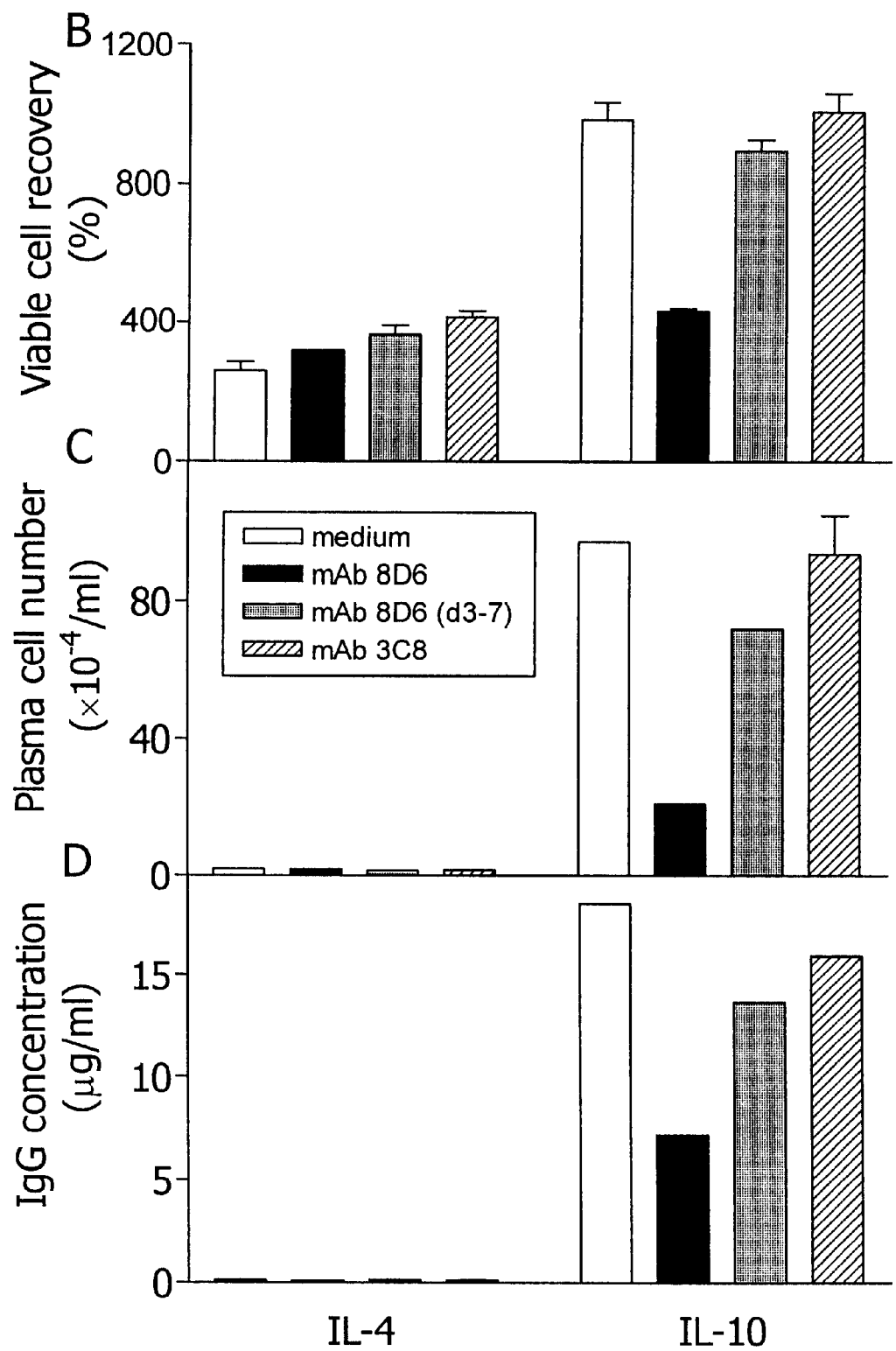
Figure 7B-D

SEQUENCE LISTING

```
<160> NUMBER OF SEQ ID NOS: 1

<210> SEQ ID NO 1
<211> LENGTH: 282
<212> TYPE: PRT
<213> ORGANISM: Homo sapiens

<400> SEQUENCE: 1

Met Ser Gly Gly Trp Met Ala Gln Val Gly Ala Trp Arg Thr Gly Ala
1               5                   10                  15

Leu Gly Leu Ala Leu Leu Leu Leu Gly Leu Gly Leu Gly Leu Glu
                20                  25                  30

Ala Ala Ala Ser Pro Leu Ser Thr Pro Thr Ser Ala Gln Ala Ala Gly
            35                  40                  45

Pro Ser Ser Gly Ser Cys Pro Pro Thr Lys Phe Gln Cys Arg Thr Ser
        50                  55                  60

Gly Leu Cys Val Pro Leu Thr Trp Arg Cys Asp Arg Asp Leu Asp Cys
65                  70                  75                  80

Ser Asp Gly Ser Asp Glu Glu Glu Cys Arg Ile Glu Pro Cys Thr Gln
                85                  90                  95

Lys Gly Gln Cys Pro Pro Pro Gly Leu Pro Cys Pro Cys Thr Gly
                100                 105                 110

Val Ser Asp Cys Ser Gly Gly Thr Asp Lys Lys Leu Arg Asn Cys Ser
            115                 120                 125

Arg Leu Ala Cys Leu Ala Gly Glu Leu Arg Cys Thr Leu Ser Asp Asp
        130                 135                 140

Cys Ile Pro Leu Thr Trp Arg Cys Asp Gly His Pro Asp Cys Pro Asp
145                 150                 155                 160

Ser Ser Asp Glu Leu Gly Cys Gly Thr Asn Glu Ile Leu Pro Glu Gly
                165                 170                 175
```

-continued

```
Asp Ala Thr Thr Met Gly Pro Pro Val Thr Leu Glu Ser Val Thr Ser
            180                 185                 190

Leu Arg Asn Ala Thr Thr Met Gly Pro Pro Val Thr Leu Glu Ser Val
        195                 200                 205

Pro Ser Val Gly Asn Ala Thr Ser Ser Ser Ala Gly Asp Gln Ser Gly
        210             215                 220

Ser Pro Thr Ala Tyr Gly Val Ile Ala Ala Ala Ala Val Leu Ser Ala
225                 230                 235                 240

Ser Leu Val Thr Ala Thr Leu Leu Leu Leu Ser Trp Leu Arg Ala Gln
                245                 250                 255

Glu Arg Leu Arg Pro Leu Gly Leu Leu Val Ala Met Lys Glu Ser Leu
            260                 265                 270

Leu Leu Ser Glu Gln Lys Thr Ser Leu Pro
        275                 280
```

MONOCLONAL ANTIBODIES THAT SUPPRESS B CELL GROWTH AND/OR DIFFERENTIATION

FIELD OF THE INVENTION

This invention relates to monoclonal antibodies which affect growth and/or differentiation of B cells in the germinal center. The monoclonal antibodies of the present invention are useful for treating disorders characterized by an abnormal growth and/or differentiation of B cells, including lymphoma, multiple myeloma and autoimmune diseases.

DESCRIPTION OF RELATED ART

As B cells mature, B cells leave the bone marrow and migrate to the lymphoid follicles of lymph nodes and spleen, and other peripheral lymphoid tissues. In the absence of antigen, mature B cells pass from blood into primary lymphoid follicles and then back into peripheral blood. If B cells encounter antigens and appropriate helper T-cells on entering the lymphoid tissue and become activated, B cells proliferate first in the T-cell areas, forming primary foci from which proliferating B cells migrate to the primary follicle forming a secondary follicle with a germinal center (or "GC").

The GC of the secondary lymphoid follicles is a unique automical site where antigen-activated B cells undergo clonal expansion and selection to differentiate into memory B cells or into antibody-secreting plasma cells. Follicular dendritic cell "FDC" is a stromal cell located in the GC which is essential for B cell growth and lymphomagenesis. The GC reaction is initiated by rapid proliferation of Ag-stimulated B cells in association with follicular dendritic cells or "FDCs" (MacLennan, I. C., *Annu. Rev. Immunol.* 12:117–139, 1994). The GC-B cells exhibit features distinct from naive or memory B cells in that GC-B cells display a unique pattern of Ag expression on the cell surface (Liu, Y. J., et al., *Immunity* 2:239–248, 1995), undergo Ag receptor-mediated apoptosis (Billian, G., P., et al., *Eur. J. Immunol.* 27:405–414, 1997), and require essential survival signals from FDCs, as disruption of FDC-B cell clusters results in apoptosis of B cells (Kosco, M. H., et al., *J. Immunol.* 148:2331–2339, 1992; Koopman, G., et al., *J. Immunol.* 152:3760–3767, 1994). Observations made using lymphotoxin-α knockout mice further confirmed that the initial interaction between FDCs and B cells is essential for GC formation (Gonzalez, M., F., et al., *J. Exp. Med.* 187:997–1007, 1998; Fu, Y.-X., et al., *J. Exp. Med.* 187:1009–1018, 1998). T cells expressing CD40 ligand (CD40L) also play a pivotal role in the GC reaction, as evidenced in hyper-IgM patients and in mouse models that have null mutations in the CD40 (Kawabe, T. et al., *Immunity* 1:167–178, 1994) or CD40L genes (Renshaw, B. R., et al., *J. Exp. Med.* 180:1889–1900, 1994).

The genetic events that occur during the clonal expansion and selection of B cells at the GC include somatic mutation and isotype switching, which leads to the production of more efficient antibodies with high affinity to the invading microorganisms. At the same time, B cell lymphoma may arise in the GC of the secondary lymphoid follicles as a consequence of genetic instability and mobility during this cellular and molecular process.

Follicular lymphoma is the most common type of non-Hodgkin's lymphoma in the west. In the early stage, follicular lymphoma is usually indolent, regressing spontaneously and showing susceptibility to chemotherapy (Horning, S. J., et al., *N. Engl. J. Med.* 311:1471–1475, 1984). However, this tumor usually recurs and can undergo blast transformation to an aggressive form, ultimately becoming a fatal disease. The generation and blast transformation of this tumor is closely associated with FDCs in the GC (Petrasch, S., et al., *Br. J. Haematol.* 80:21–26, 1992).

Multiple myeloma is a tumor usually found in bone marrow. Myeloma cells grow aggressively and, like plasma cells (PCs) from which myeloma cells are believed to originate, secrete immunoglobulins. PCs are generated in the GC as a result of clonal expansion and selection, during which process somatic mutation and isotype switching occur. PCs then migrate to bone marrow to expand in the presence of stroma cells. As a consequence of the genetic mobility and mutability involved in the generation and translocation of PCs, malignant transformation may occur which leads to the development of multiple myeloma.

The present invention provides monoclonal antibodies which interfere with the interactions between FDCs and B cells, thereby suppressing the growth and/or differentiation of B cells, as well as tumorigenesis of B cells in vivo. The monoclonal antibodies of the present invention are useful for treating disorders characterized by an abnormal growth and/or differentiation of B cells, including lymphoma, multiple myeloma and autoimmune diseases.

SUMMARY OF THE INVENTION

A preferred monoclonal antibody of the present invention is mAb 8D6. The hybridoma cell line which produces mAb 8D6 was deposited on Mar. 13, 2001 with the American Type Culture Collection, 10801 University Boulevard, Manassas, Va. 20110-2209 (ATCC deposit number designated as PTA-3231)

Another preferred monoclonal antibody of the present invention is mAb 4G10. The hybridoma cell line which produces mAb 4G10 was deposited on Mar. 13, 2001 with the American Type Culture Collection, 10801 University Boulevard, Manassas, Va. 20110-2209 (ATCC#).

Hybridoma cell lines which produce mAb 8D6 and mAb 4G10, respectively, are provided in another embodiment of the present invention.

Functional derivatives of the monoclonal antibodies of the present invention are also provided, including, but not limited to, Fab, Fab', F(ab')$_2$, single chain antibodies, chimeric antibodies and the like.

Another embodiment of the present invention is directed to pharmaceutical compositions. The pharmaceutical compositions include a monoclonal antibody of the present invention or a functional derivative thereof, and a pharmaceutically acceptable carrier.

A further aspect of the invention provides methods of treating a subject suffering a pathological condition characterized by abnormal B cell growth or differentiation by administering to the subject a therapeutically effective amount of a monoclonal antibody of the present invention or a functional derivative thereof. Pathological conditions which can be treated by practicing the present methods include lymphoma, multiple myeloma and autoimmune diseases.

BRIEF DESCRIPTION OF DRAWINGS

FIGS. 7A–7D depict the stimulation of plasma cell (PC) generation by FDC-signaling molecule-8D6 (FDC-SM-8D6).

DETAILED DESCRIPTION OF THE INVENTION

Figure 1:
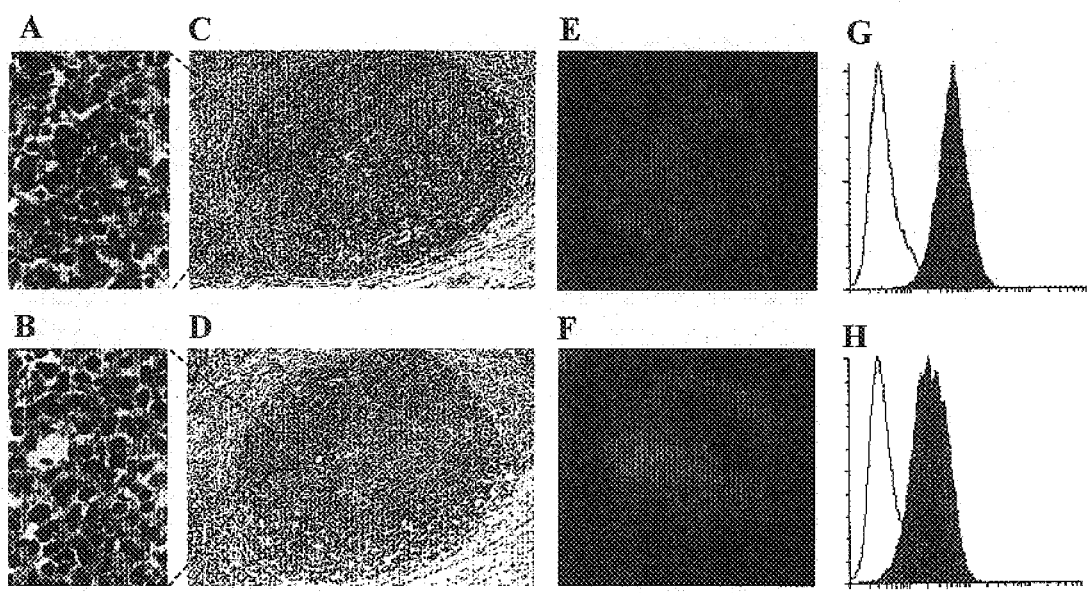
FIGS. 1A–1F depict immunohistological localization of 8D6 Ag expression in human FDCs. The serial cryostat sections from a normal human tonsil (C and D) or cytospin preparations of human tonsil FDC clusters (E and F) were stained with mAbs 8D6 (A, C, and E), DRC-1 (B and D), and 7D6 (F). A and B are higher power views of boxed areas in C and D, respectively, showing the network staining pattern. Original magnifications: (C and D)×100; (E and F)×1,000.
FIGS. 1G–1H depict the expression of 8D6 Ag on HK cells. HK cells were stained with mAbs 8D6 (G, filled histogram), 3C8 (H, filled histogram), or isotype control mouse IgG1 (G and H, open histograms), followed by FITC-conjugated goat anti-mouse IgG. FITC intensity was analyzed by FACScan™.

One embodiment of the present invention is directed to monoclonal antibodies which suppress the growth and/or differentiation of B cells in the lymphoid follicles.

Without intending to be limited to any particular theory, the inhibitory effects of the instant monoclonal antibodies are believed to be achieved by interfering with the interactions between follicular dendritic cells (FDCs) and B cells, as the proliferation and differentiation of B cells in the lymphoid follicles depend on interactions of B cells with FDCs. The term "interaction" encompasses interactions mediated by direct cell-cell contact, as well as interactions mediated by molecules secreted by FDCs that directly or indirectly affect the proliferation and differentiation of B cells in the lymphoid follicles.

The monoclonal antibodies of the present invention can be generated essentially as follows. An animal (e.g., mouse, sheep or rabbit) is immunized with isolated human FDCs. The animal is preferably neonatally tolerized with human tonsillar mononuclear cells (MNCs) prior to the immunization with human FDCs. Spleen cells are isolated from the immunized animal and used in fusion with myeloma cells for making hybridomas. Hybridomas that make monoclonal antibodies capable of inhibiting FDC-dependent B cell growth or differentiation are then identified and cloned.

Preferred monoclonal antibodies of the present invention are mAb 8D6 and mAb 4Gb10. The hybridoma cell lines that produce mAb 8D6 (ATCC deposit number designated as PTA-3231) and mAb 4G10 (ATCC deposit number designated as PTA-3230), respectively, were deposited on Mar. 13, 2001 with American Type Culture Collection (ATCC).

Hybridoma cell lines which produce mAb 8D6 and mAb 4G10 form another embodiment of the present invention.

These hybridomas represent preferred sources for preparing mAb. 8D6 and mAb 4G10. Monoclonal antibodies can be purified from culture supernatant of the hybridomas grown in tissue culture flasks. Alternatively, hybridoma cells can be injected into animals to produce inflammatory ascites. Antibody-containing ascites can be harvested 8–12 days after intraperitoneal injection. The ascites contain a higher concentration of antibodies, but include both monoclonals and immunoglobulins from the animal.

Monoclonal antibodies in the hybridoma supernatant or in the ascites can be purified by a variety of conventional protein purification methods, for example, affinity chromatography. Alternatively, hybridoma supernatant or the ascites can be used directly in place of the monoclonal antibodies under certain circumstances. Those skilled in the art can determine whether purification of the monoclonal antibodies is required for a particular use.

Another embodiment of the present invention is directed to functional derivatives of the monoclonal antibodies of the present invention. "Functional derivatives" refer to antibody molecules or fragments thereof which are derived from a monoclonal antibody of the present invention and which have retained the antigenic specificity and the functional activity (i.e., inhibiting FDC-dependent proliferation and/or differentiation of B cells) of the original monoclonal antibody. Examples of functional derivatives include Fab, Fab', F(ab')$_2$ of the present mAbs, single chain antibodies, chimeric antibodies and the like.

Techniques which can be employed for making Fab, Fab', and F(ab')$_2$ fragment of an antibody are well known in the art. See, e.g., Coligan et al. *Current Protocols in Immunology*, John Wiley & Sons Inc., New York, N.Y. (1994); Harlow, E. and Lane, D., *Antibodies: A Laboratory Manual*, Cold Spring Harbor Press, 1988.

A single-chain antibody (sAb) is created by fusing together the variable domains of the heavy and light chains using a short peptide linker, thereby reconstituting an antigen-binding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. *J. Biol. Chem.*, 265:18615 (1990); Chaudhary et al. *Proc. Natl. Acad. Sci.*, 87:9491 (1990); U.S. Pat. No. 4,946,778 to Ladner et al.; and U.S. Pat. No. 5,359,046 to Capon et al.

Chimeric antibodies as used herein refer to antibodies which contain the antigen-binding portion of the murine monoclonal antibodies of the present invention and a portion of an immunoglobulin from another species. For example, a chimeric antibody of the present invention can contain the variable region of mAb 8D6, joined to the constant region of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication #PCT/US86/02269 (published May 7, 1987); Liu et al., *Proc. Natl. Acad Sci. USA* 84:3439–3443 (1987); Sun et al., *Proc. Natl. Acad. Sci. USA* 84:214–218 (1987); Better et al., *Science* 240:1041–1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes. Humanized chimeric antibodies can also be made by constructing a reshaped human antibody, which has been described in, e.g., Maeda et al., *Hum. Antibod. Hybridomas* 2: 124–134 (1991), and Padlan, *Mol. Immunol.* 28: 489–498 (1991).

A derivative of the monoclonal antibodies of the present invention can be tested to determine whether such derivative possesses the antigenic specificity and the functional activity of the original monoclonal antibody. Antigenic specificity can be assessed in assays, e.g., staining of FDCs or HK cells, or Western Blot analysis using FDC-SM-8D6. The functional activity of a derivative can be assessed in assays, e.g., coculturing GC-B cells with FDCs or HK cells with or without the derivative in the presence of CD40L, rIL2, rIL10 and assaying for B cell growth and/or differentiation.

A further aspect of the invention is directed to pharmaceutical compositions which include a monoclonal antibody of the present invention, or a functional derivative thereof, or combinations thereof. Preferred monoclonal antibodies for use in the pharmaceutical compositions of the present invention are mAb 8D6 and mAb 4G10.

The pharmaceutical compositions of the present invention can include other substances such as cytokines, adjuvants and pharmaceutically acceptable carriers. As used herein, a pharmaceutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art.

A further aspect of the invention is directed to methods of treating subject suffering a pathological condition characterized by abnormal growth or differentiation of B cells. In accordance with the present invention, the subject is treated by administration of a therapeutically effective amount of an antibody of the present invention.

By "treating" is meant that the abnormal growth or differentiation of B cells is inhibited, reduced, or eliminated, or the occurrence of the abnormality of B cell growth or differentiation is prevented or delayed.

A "subject" which can be treated in accordance with the present methods can be any mammalian subject, including humans, dogs, monkeys, cows and the like. A preferred subject to be treated is a human individual.

Pathological conditions which can be treated in accordance with the present invention include lymphoma, multiple myeloma and autoimmune diseases such as rheumatoid arthritis, systemic lupus erythematous and multiple sclerosis.

Preferably, the present method is employed to treat patients suffering lymphoma, including both Hodgkin's and non-Hodgkin's lymphoma that are follicular lymphoma or diffuse large B cell lymphoma. These lymphomas are most common type of lymphomas in adults in the West.

Preferred antibodies for use in the administration include mAb 8D6, mAb 4G10, a functional derivative of such monoclonal antibodies, or a combination thereof. More preferably, a combination of mAb8D6 and mAb 4G10, or a combination of functional derivatives (e.g., humanized antibodies) of mAb8D6 and mAb 4G10, is administered to the subject.

An antibody can be administered alone or together with a pharmaceutically acceptable carrier. A pharmaceutically acceptable carrier includes all solvents, such as fats, oils, water, saline solutions, lipids, liposomes, resins, binders, fillers, dispersion media, cell culture media, and the like, or combinations thereof, that are non-toxic to the recipient subject.

In accordance with the present invention, an antibody or an antibody derivative can be combined with the carrier in any convenient and practical manner, e.g., by solution, suspension, emulsification, admixture, encapsulation, absorption and the like, and if necessary, by shaping the combined compositions into pellets or tablets. Such procedures are routine for those skilled in the art.

Dosages of an antibody or an antibody derivative to be therapeutically effective depend on the disease state and other clinical factors, such as weight and condition of the subject, the subject's response to the therapy, the type of formulations and the route of administration. The precise dosage of an antibody to be therapeutically effective can be determined by those skilled in the art. As a general rule, the therapeutically effective dosage of an antibody can be in the range of about 0.5 µg to about 2 grams per unit dosage form, or preferably, about 0.5 µg to about 1 mg per unit dosage form. A unit dosage form refers to physically discrete units suited as unitary dosages for mammalian treatment: each unit containing a pre-determined quantity of the active material calculated to produce the desired therapeutic effect in association with any required pharmaceutical carrier. The methods of the present invention contemplate single as well as multiple administrations, given either simultaneously or over an extended period of time.

The administration of an antibody may be carried out in any convenient manner, including by aerosol inhalation, injection, ingestion, transfusion, implantation or transplantation. Preferably, the antibodies of the present invention are administered to a patient by injection, and more perferably subcutaneous (s.c.), intraperitoneal (i.p.), intra-arterial (i.a.), or intravenous (i.v.) injection. Preferably, the injection is near the tumor site if possible.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

The present invention is further illustrated by the following examples.

EXAMPLE 1

Antibodies

Abs used in the following examples were anti-CD40 (G28-5; American Type Culture Collection); DRC-1 (clone R4/23; DAKO, Carpinteria, Calif.); 7D6 (from. Dr. Yong-Jun Liu, Laboratory for Immunological Research, Schering-Plough Corp., Dardilly, France); isotype matched control mAb 3C8 ($IgG_1$) (Choe et al., *J. Immunol.* 157:1006, 1996); biotin-conjugated goat anti-mouse Ig or horseradish peroxidase-conjugated goat anti-human IgG (BioSource International, Camarillo, Calif.); streptavidin-biotinylated horseradish peroxidase complex (Amersham Life Science, Piscataway, N.J.); FITC-conjugated goat anti-mouse IgG (PharMingen); rabbit anti-human IgG or alkaline phosphatase-conjugated rabbit anti-mouse IgG (ICN Biomedi-cals); horseradish peroxidase conjugated goat anti-human IgG (Cappel pharmaceutical, Inc. Malvern, Pa.); anti-CD44 (NKI-P1, $IgG_1$, Dr. C. G. Figdor, University Hospital Nijmegen, Nijmegan, The Netherlands); rat anti-mouse $IgG_1$, microbeads (Miltenyi Biotech Inc., Sunnyvale, Calif.); and FITC-conjugated anti-CD20, PE-conjugated anti-CD38, and FITC-conjugated goat anti-mouse Ig (Pharmingen, San Diego, Calif.).

Cell Lines, Cytokines and Reagents

Tonsillar B cells were prepared and GC-B cells were isolated by magnetic cell separation (MACS; Miltenyi Biotec) as described by Choe et al. (*J. Immunol.* 157:1006–1016, 1996). Fresh FDC clusters were isolated from tonsils of 3–10-yr-old children as described by Choe et al. (*J. Immunol* 164:56–63, 2000). The FDC line, HK, was established and maintained as described by Kim et al. (*J. Immunol.* 155:1101–1109, 1995). The L3055 cell line was cocultured with HK cells in IMDM (Irvine Scientific) supplemented with 10% FCS (Life Technologies), 2 mM glutamine, 100 U/ml penicillin G, and 100 mg/ml streptomycin (Irvine Scientific). GC-B cells were culture in Iscove's modified Dulbecco's medium (Irvine Scientific, Santa Ana, Calif.) supplemented with 10% fetal calf serum (Life Technologies, Inc., Grand Island, N.Y.), 2 mM glutamine, 100 U/ml penicillin G, and 100 µg/ml streptomycin (Irvine Scientific).

Annexin V-FITC apoptosis detection kit was purchased from Trevigen. Cytokines used in the following examples were CD40L (Immunex Corp.), recombinant human (rh) IL-2 (Hoffman-La Roche), rhIL-10 (R&D Systems), rhIL-4 (Schering-Plough Corp.), and rhIL-6 (Sandoz Research Institute).

EXAMPLE 2

Generation of mAbs Staining FDCs

Murine mAbs that react to human tonsillar FDCs were generated using a procedure that involved tolerization before immunization (Golumbeski et al., *Anal. Biochem.* 154:373–381, 1986). Tolerization was achieved by injection of newborn (within 40 h after birth) BALB/c mice with tonsillar mononuclear cells (MNCs) containing human T and B cells. At 2 month of age, this animal was injected intraperitoneally with freshly isolated FDC clusters ($2 \times 10^4$) three times in a 2-week interval. After the third immunization, the serum from the immunized mouse showed strong reactivity to tonsillar FDCs in frozen tissue sections, but no reactivity to MNCs as assayed by the cell-based ELISA. Spleen cells from this mouse were used as fusion partners with a mouse myeloma cell line, SP 2/0, to generate mAbs. After the cell fusion, more than 600 hybridomas were grown, and their supernatants were screened for FDC staining as follows. The adjacent cryostat sections of a human tonsil were fixed in cold acetone. Slides were blocked with 1% (wt/vol) BSA-PBS, then incubated with supernatants from hybridomas, followed by FITC-conjugated goat anti-mouse Ig, then observed under the fluorescence microscope. The hybridoma supernatants containing more than 10 mg/ml of mouse Ig were subjected to ELISA which tested for reactivities to MNCs. The hybridomas reacting to MNCs were discarded. The hybridomas that were negative in MNC-based ELISA were subjected to the next screening step: HK binding by ELISA and immunohistochemical staining of the frozen sections of the tonsillar tissues. These screening steps were repeated during a limiting dilution procedure to select a single mAb-producing clone.

Twenty-eight (28) hybridomas were identified that specifically stained the tonsillar GC. Of 28 hybridomas, 17 mAb clones were obtained by a limiting dilution method. 16 IgG mAbs were purified from ascites by affinity chromatography with protein A/G. One of these mAbs, an IgG1 called 8D6, recognized a molecule expressed in human tonsillar GCs (FIGS. 1, A and C) with an immunohistochemical staining pattern similar to that of the known FDC-specific mAb, DRC-1 (FIGS. 1, B and D). Monoclonal Ab DRC-1 has been described by Naiem, M., et al. (*J. Clin, Pathol.* 36:167–175, 1983). The mAb 8D6 staining was restricted to the follicles (FIG. 1C). There is a clear demarcation between the GC and the T cell-rich area outside of the GC, which is negative for all three mAbs (e.g., DRC-1, 7D6, and 8D6). The 8D6 Ag is abundantly expressed in the GC, staining the reticular network in the higher magnification (FIG. 1A). The diffuse staining pattern of mAb 8D6 in the GC is characteristic of FDCs surrounding MNCs in the follicles. Such a staining pattern was confirmed by the simultaneous staining of the adjacent tissue sections with known FDC-specific mAbs such as DRC-1 (FIG. 1B) and 7D6. mAb 7D6 has been described by Liu et al. (*J. Exp. Med.* 185:165–170, 1997). A single cell suspension was prepared as a cytospin. The cytospin preparations were stained with FDC-staining mAbs and examined under the microscope. At the single cell level, mAbs 8D6 (FIG. 1E) and 7D6 (FIG. 1F), both stained large, cytoplasm-rich, sometimes binucleated FDCs. The isotype-matched control Abs did not stain FDCs, excluding the possibility of autofluorescence.

Another mAb of the 16 mAbs, 4G10, also specifically stained FDCs in the GC. Both mAb 8D6 and mAb 4G10 showed positive binding to HK cells when analyzed by FACS.

EXAMPLE 3

Functional Blocking Activity of FDC-Specific mAb 8D6 in FDC-B Cell Interaction

To measure its ability to block FDC-B cell interaction, mAb 8D6 was used in the coculture of B cells and FDC clusters. Because Ag-activated T cells participate in GC reactions by direct cell-to-cell contact and by secreting cytokines (Han, S., et al., *J. Immunol.* 155:556–567, 1995), the defined signals of activated T cells, such as anti-CD40, IL-2 and IL-10, were used to characterize mAb 8D6 functions.

Figure 2:
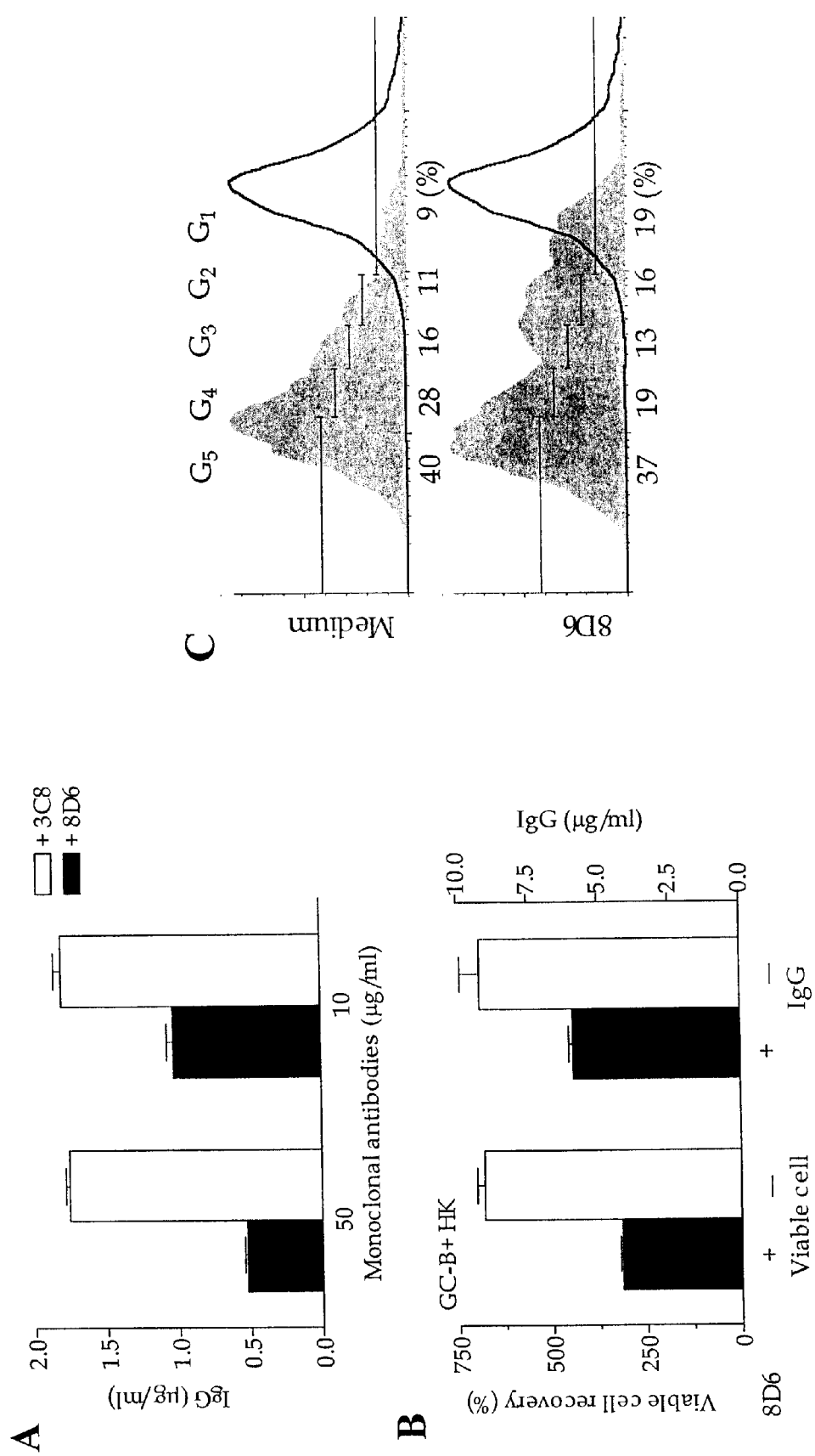
FIGS. 2A–2C depict inhibition of FDC-B cell interaction by mAb 8D6. (2A) Tonsillar B cells were cocultured with irradiated FDC clusters (2,000 clusters per well; 5,000 rads) for 10 d in the presence of mAb 8D6 or 3C8, anti-CD40 (100 ng/ml), rhIL-2 (10 U/ml), and rhIL-10 (30 ng/ml). IgG levels in conditioned media were measured by human IgG-specific ELISA. IgG concentrations in the control cultures with B cells and B cells plus FDCs were 0.26 and 1.8 mg/ml, respectively. (2B and 2C) GC-B cells were cocultured with or without mAb 8D6 in the presence of irradiated HK cells, CD40L, rhIL-2, and rhIL-10. Results of viable cell recovery (2B, left), IgG secretion (2B, right), and cell cycle progression (2C) are shown.

Tonsillar B cells were cocultured with irradiated FDC clusters (2,000 clusters per well; 5,000 rads) for 10 days in the presence of mAb 8D6 or 3C8, anti-CD40 (100 ng/ml), rhIL-2 (10 U/ml), and rhIL-10 (30 ng/ml). IgG levels in conditioned media were measured by human IgG-specific ELISA. IgG concentrations in the control cultures with B cells and B cells plus FDCs were 0.26 and 1.8 mg/ml, respectively. As can be seen from FIG. 2A; mAb 8D6 consistently inhibited the FDC-mediated B cell IgG secretion. The blocking activity of mAb 8D6 is specific because another FDC-specific murine IgG1, mAb 3C8, did not inhibit the FDC costimulatory activity (FIG. 2A). Monoclonal Ab 3C8, as described by Choe et al. (*J. Immunol.* 157:1006–1016, 1996), was prepared by immunizing mice with HK cells, and its Ag was abundantly expressed in FDC and HK cells (FIG. 1H). In addition to mAb 3C8, the other 13 IgG1, FDC-specific mAbs prepared in parallel with mAb 8D6 did not show blocking activity. Furthermore, five other known human FDC-specific mAbs obtained by various investigators, namely DRC-1 (Naiem, M., et al., *J. Clin, Pathol.* 36:167–175, 1983), 7D6 (Liu et al., *J. Exp. Med.* 185:165–170, 1997), HJ-2 (Butch et al., *Cell. Immunol.* 155: 27, 1994), GP93 (Farace et al., *Eur. J. Immunol.* 16: 1521, 1986), and Ki-M4 (Parwaresch et al., *Blood* 62: 585, 1983), did not inhibit the FDC costimulatory activity in the assay.

In a separate experiment, GC-B cells were cocultured with or without mAb 8D6 in the presence of irradiated HK cells, CD40L, rhIL-2, and rhIL-10. HK is a human FDC line which resembles primary FDCs in the ability to rescue GC-B cells from apoptosis (Kim, H.-S, et al., *J. Immunol.* 155:1101–1109, 1995) and to support GC-B cell growth and differentiation (Choe, J., et al., *J. Immunol.* 157:1006–1016, 1996). GC-B cells ($10^6$ cells/ml) were cocultured with irradiated HK cells ($2 \times 10^4$ cells per well; 5,000 rads) in 24-well plates with or without mAb 8D6 (10 mg/ml) in the presence of CD40L (100 ng/ml), rIL-2 (10 U/ml), and rIL-10 (20 ng/ml) for 2 days, washed, and then recultured ($2 \times 10^5$ cells/well) with irradiated HK cells for another 4 days. Viable cells were counted by trypan blue exclusive assay for proliferation. For differentiation, triplicate culture supernatants were harvested and pooled, and IgG concentrations were measured by ELISA as described by Li et al. (*Cell. Immunol.* 168:133–140, 1996). As shown in FIG. 2B, GC-B cell proliferation and differentiation supported by HK cells were inhibited by the addition of mAb 8D6, but not by the isotype control mAb 3C8.

The cell cycle progression of the CFSE-labeled GC-B cells after activation by soluble CD40L was also inhibited by the addition of mAb 8D6. For cell cycle analysis, GC-B cells were labeled with carboxyfluorescein diacetate succinimidyl ester (CFSE, 5 mM/ml in PBS; Sigma Chemical Co.) at 48° C. for 10 min. Labeled GC-B cells were then cocultured with or without mAb 8D6 in the presence of irradiated HK cells, CD40L, rhIL-2, and rhIL-10, as described above. After culture for 6 days, the CFSE intensity was analyzed by FACScan™. As shown in FIG. 2C, 19% of GC-B cells remained in the first generation (G1) when mAb 8D6 was present in the culture, as relative to 9% in the absence of mAb 8D6; 16% of GC-B cells remained in the second generation (G2), compared to 11% in the absence of mAb 8D6. This result indicates that mAb 8D6 exerts its inhibitory effect by delaying B cell proliferation, rather than by direct cell killing.

EXAMPLE 4

The Growth Inhibition of Lymphoma Cell Line, L3055, by mAb 8D6 and mAb 4G10.

GC-B cells undergo complex interactions with FDCs and T cells in the course of differentiation into memory B and plasma cells. GC-B cells freshly isolated from tonsils are heterogeneous with respect to the stage of differentiation, mutation frequency, and Ig class (Pascual, V., et al., *J. Exp. Med.* 180:329–339, 1994). To delineate the individual roles of FDCs and T cells in GC-B cell differentiation at the clonal level, a unique experimental model was developed which employed the FDC line, HK, and a Burkitt's lymphoma cell line, L3055. L3055 cell line resembles normal centroblasts and represents a clonal population originating from the GC (Choe et al., *J. Immunol.* 164:5643, 2000).

Figures 3A, 3C:
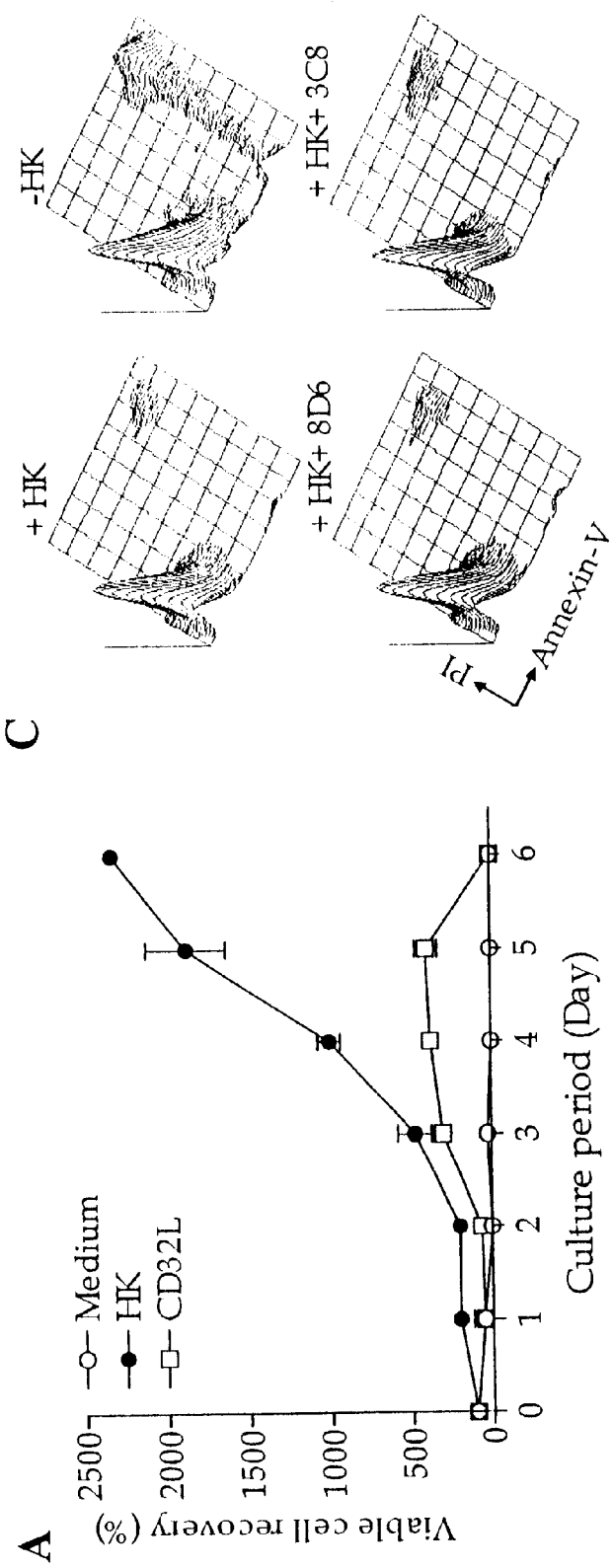
FIGS. 3A–3C depict the inhibition by mAb 8D6 of HK-dependent L3055 cell proliferation. HK-dependent L3055 cells ($2\times10^4$ cells/ml) were cultured in the presence of irradiated HK or CD32-transfected L cells ($2\times10^4$ cells per well; 5,000 rads) for the indicated time periods in 24-well plates (3A). In a separate experiment (3B), L3055 cells ($2\times10^4$ cells/ml) were cultured for 5 days with irradiated HK cells ($2\times10^4$ cells per well; 5,000 rads) pretreated with culture medium alone (control), mAb 8D6, mAb 4G10, or a combination of mAb 8D6 and mAb 4G10 (20 µg/ml each). Viable cells were counted by trypan blue exclusion assay, and viable cell recovery percentages are shown. (3C) L3055 cells ($10^4$ cells/ml) were cultured in the presence or absence of irradiated HK cells for 24 h. HK cells were pretreated with mAbs 8D6 or 3C8 for blocking experiments. Cultured cells were stained with FITC-labeled annexin V and propidium iodide.
Figure 3:
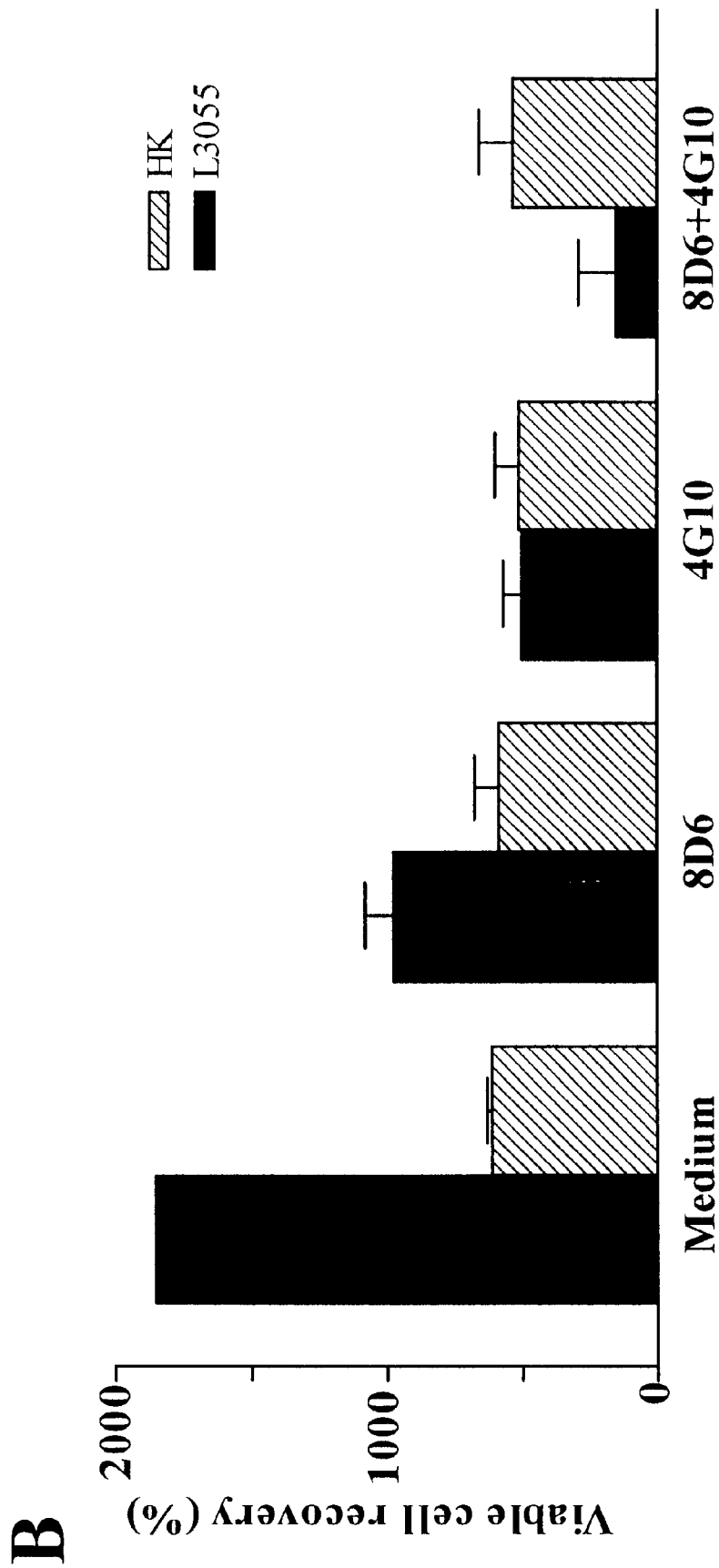

Like freshly isolated centroblasts, L3055 cells underwent spontaneous apoptosis when cultured in the absence of fresh FDCs or HK cells. However, when L3055 cells ($2 \times 10^4$ cells/well) were cultured in the presence of irradiated HK cells ($2 \times 10^4$ cells per well; 5,000 rads), L3055 cells proliferated continuously (FIG. 3A). Unlike HK cells, irradiated CD32-transfected L cells ($2 \times 10^4$ cells per well; 5,000 rads) did not support the growth of L3055 (FIG. 3A), indicating that the growth-supporting activity of HK cells was not a specific feeder cell effect.

In a separate experiment, L3055 cells ($2 \times 10^4$ cells/ml) were cultured for 5 days with irradiated HK cells ($2 \times 10^4$ cells per well; 5,000 rads) which had been pretreated with mAb 8D6, mAb 4G10, or a combination of mAb 8D6 and mAb 4G10 (20 μg/ml each). At the end of the 5-day culture, viable L3055 cells were counted by trypan blue exclusion assay, and viable cell recovery percentages are shown in FIG. 3B. The growth-supporting activity of HK cells in this coculture was decreased by the addition of mAb 8D6 or 4G10 (FIG. 3B).

To determine whether mAb 8D6 affected apoptosis, L3055 cells ($10^4$ cells/ml) were cultured in the presence or absence of irradiated HK cells for 24 h. HK cells were pretreated with mAbs 8D6 or 3C8 for blocking experiments. Cells were stained with FITC-labeled annexin V and propidium iodide, and the percentage of viable cells were calculated. As shown in FIG. 3C, mAb 8D6 did not interfere with the capacity of HK cells to prevent spontaneous apoptosis.

EXAMPLE 5

Cloning and Expression of cDNA Encoding 8D6 Ag

As the HK cells expressed the 8D6 Ag (FIG. 1G), a cDNA expression library was prepared from the HK cells. The cDNA library was screened by in situ staining of transiently transfected COS cells with the mAb 8D6. A cDNA clone encoding the 8D6 Ag was isolated and the encoded amino acid sequence of 282 residues was set forth in SEQ ID NO: 1. The protein, named as "FDC-SM-8D6" ("SM" for signaling molecule), has a putative signal peptide (Met1-Gly30) and a predicted transmembrane domain (Ile232-L250). There are three consensus sites (Asn126, Asn195 and Asn213) for N-linked glycosylation.

The functional activity of FDC-SM-8D6 in B cell costimulation was analyzed in vitro by using transfected COS cells. COS cells ($2\times10^5$/well) in 6-well plates were transfected with 2 mg 8D6 Ag cDNA and the LipofectAMINE™ reagent. After 24 h, transfected COS cells were used for coculture with tonsillar B cells ($10^6$/ml) in the presence of anti-CD40 (100 ng/ml), rhIL-2 (10 U/ml), rhIL-4 (50 U/ml), rhIL-6 (20 ng/ml), and rhIL-10 (20 ng/ml) for 24 h. Activated B cells were removed from COS cells, recultured in triplicate in 96-well plates in the presence of the above cytokines, and subjected to proliferation (3 day) or differentiation (10 day) assays as described above.

Figure 4:
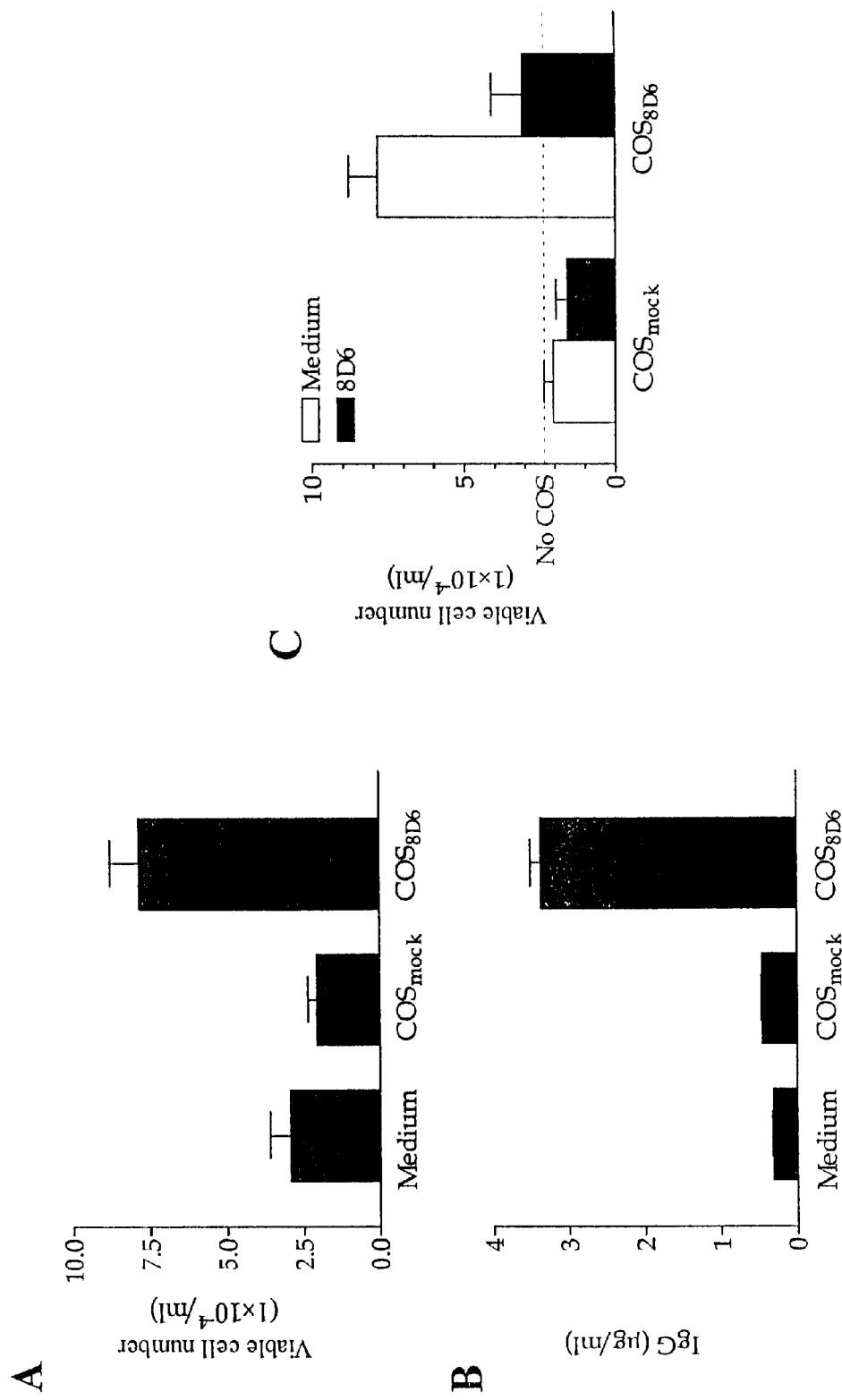
FIGS. 4A–4C depict stimulation of B cell proliferation and differentiation by 8D6 Ag cDNA-transfected COS cells. Mock ($COS_{Mock}$) or 8D6 Ag cDNA ($COS_{8D6}$)-transfected COS cell-B cell cocultures were performed. The viable cell number of B cells (4A) and IgG secretion data (4B) was shown. In blocking experiments, transfected COS cells were treated with mAb 8D6 for 30 min at 37° C. before coculture with B cells (4C).

As shown in FIGS. 4A–4C, in the cocultures with anti-CD40-activated B cells, the FDC-SM-8D6-transfected COS cells enhanced B cell proliferation (FIG. 4A) and differentiation by inducing IgG secretion (FIG. 4B) two to seven times higher than the mock-transfected COS cells. In addition, this activity was specifically blocked by mAb 8D6 (FIG. 4C), but not by the control Ab with the same isotype. Thus, FDC-SM-8D6 expressed by COS cells was able to provide a specific costimulatory signal in augmenting growth and differentiation of GC-B cells.

EXAMPLE 6

Inhibition of B Cell Lymphomagenesis in vivo by mAb 8D6 and mAb4G10

Figure 5:
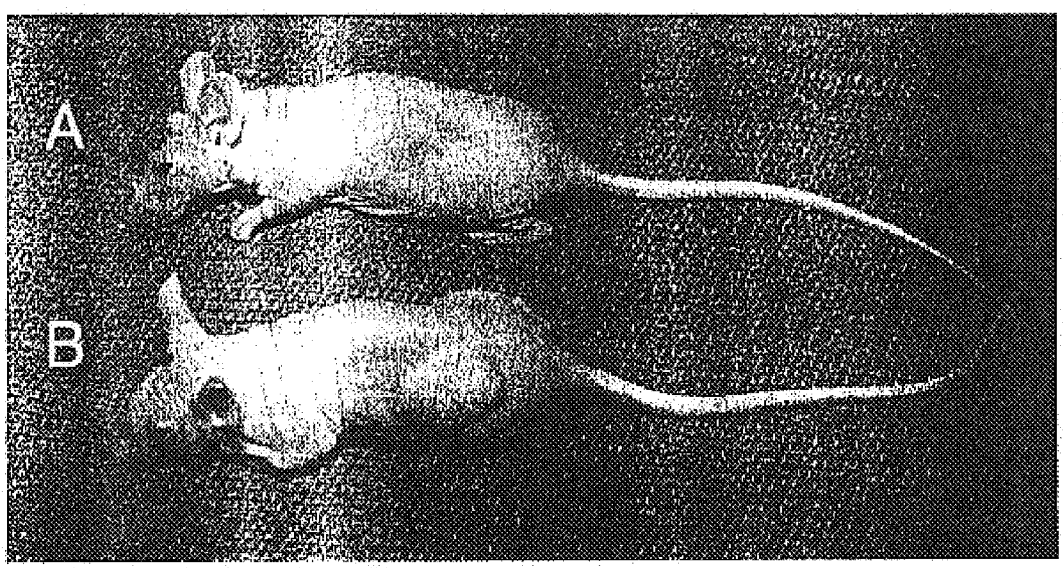
FIGS. 5A–5B depict lymphoma formation in the presence of HK cells. Nude mice were subcutaneously (s.c.) injected using L3055 cells without (5A) or with (5B) HK cells. Images were taken 60 days after inoculation.

Solid tumors were formed when L3055 cells ($2\times10^6$ cell/site) and HK cells ($1\times10^6$ cell/site) were subcutaneously (s.c.) inoculated into nude mice (FIG. 5B). The s.c. injected cells produced local progressively growing tumor masses at the injection site without distant metastasises in nude mice. There was no tumorigenesis when either L3055 (FIG. 5A) or HK cells alone were injected. The failure of tumorigenesis was not attributed to the inoculation period of 60 days. There was no tumor formed if the inoculation period was longer than 4 months.

HK cell titration experiments showed that tumors could form when a lower dose of HK cells ($5\times10^5$ cell/site) was co-inoculated with L3055 cells. When a fixed number of HK cells ($1\times10^6$ cell/site) were injected with increasing number of L3055 cells, tumor formation was observed in a shortened time frame. In contrast, no tumor was formed when increasing numbers of L3055 cells up to $4\times10^6$ cell/site were injected alone. These results indicate that the lack of tumor formation when L3055 cells were injected alone did not result from an insufficient number of injected cells.

FACS analysis of tumor cell surface markers were performed to identify the origin of the tumor mass. L3055 cells express high levels of CD38 but no CD44, while CD44 is a marker for HK cells. The results from FACS analysis showed that the tumor cells were $CD20^+CD38^+CD44^-$, confirming that the tumor cells originated from the injected L3055 cells, not from cells of murine origin. In addition, immunohistochemistry staining of tumor tissue biopsy indicated that the tumor cells were $CD38^+CD44^-$, which is identical phenotype to L3055 cells inoculated.

Figure 6A:
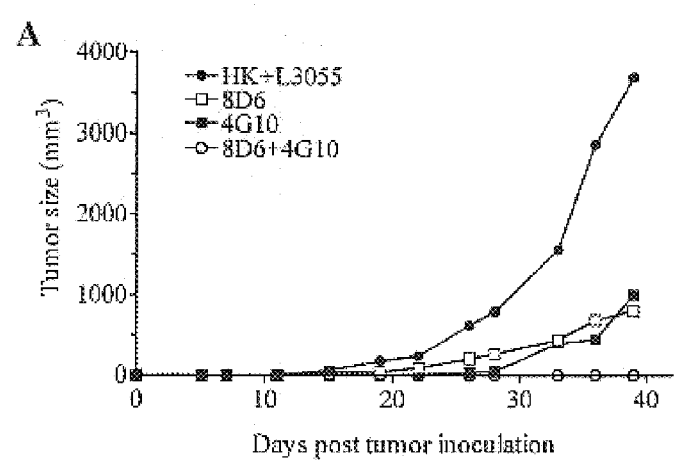
FIGS. 6A–6C depict the inhibition of lymphoma formation in nude mice by FDC-binding mAbs. 6A. L3055 cells and FDC-binding mAbs pretreated HK cells were inoculated into nude mice. The size of solid tumor was measured twice a week with a caliber and expressed in volumn (volumn= length×width×height, in $mm^3$). A tumor growth curve of a typical experiment was shown. 6B. A summary of in vivo xenoraft experiments. The number of experiment and the size of tumor formed on day 60 were shown. 6C. A photo of nude mice inoculated as described in 6A at day 38. Cells and mAbs injected were as follows: 1, HK+L3055; 2, HK+L3055+8D6; 3, HK+L3055+4G10; and 4, HK+L3055+ 8D6+4G10.
Figure 6B:
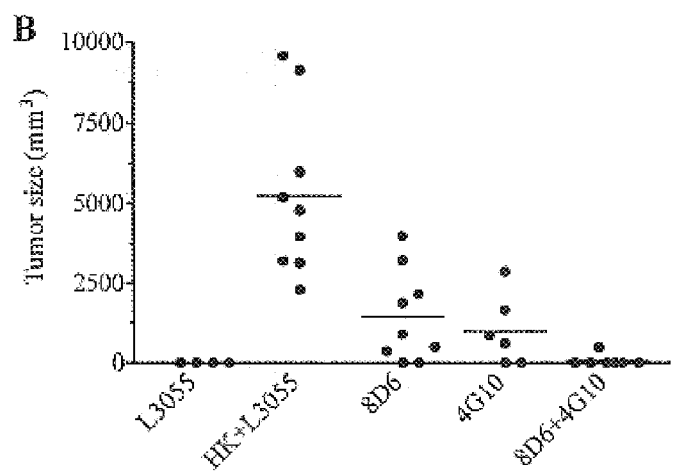
Figure 6C:
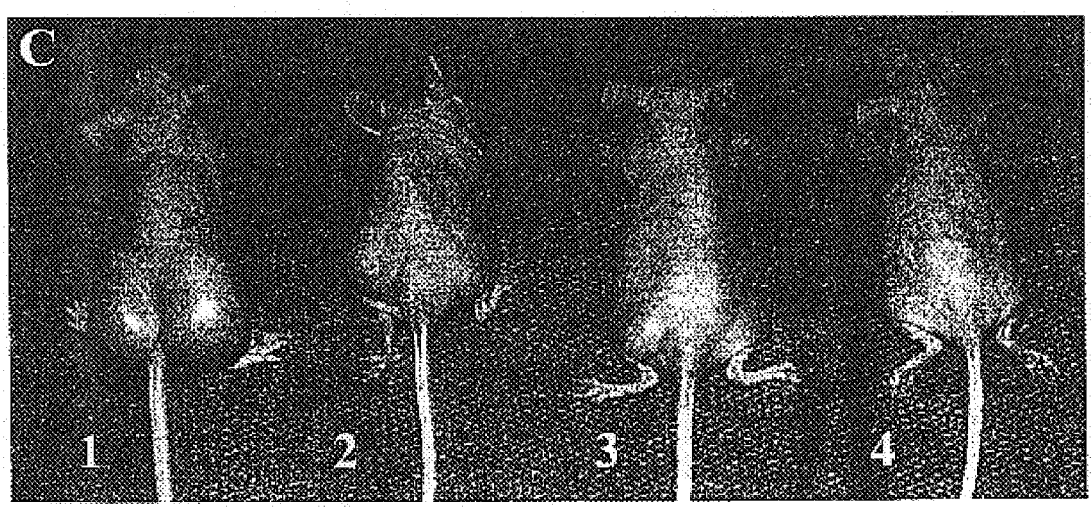

To determine the effect of mAbs 8D6 and 4G10 on lymphoma formation, mAb 8D6 or mAb 4G10 was injected into mice together with L3055 cells and HK cells. The volumes of solid tumors were measured at different time points. As shown in FIG. 6A, both mAb 8D6 and mAb 4G10 delayed lymphoma formation. At 38 days after injection, tumors formed in the presence of mAb 8D6 (FIG. 6C(2)) were smaller than those in the control animals formed without mAb8D6 (FIG. 6C(1)). Only one tumor out of two injection sites was formed in the presence of mAb 4G10 (FIG. 6C(3)). No tumor was formed when both of the mAbs were added (FIG. 6C(4)). As summarized in FIG. 6B, the differences in tumor size between the control group and the group with mAb 8D6 (p=0.0014) or 4G10 (p=0.0023) pre-treated HK cells were statistically significant. In addition, the inhibitory effect of the combination of mAbs 8D6 and 4G10 on tumorigenicity of L3055 cells, relative to the effect of the control antibody, was also statistically significant effect (p=0.0001).

EXAMPLE 7

FDC-SM-8D6 Stimulates PC Generation, But Not Memory B Cell Proliferation

Kinetic experiments revealed that cytokines secreted by activated T cells determined the pathway of GC-B cell differentiation. IL-4 directed GC-B cells to differentiate into memory B cells, whereas IL-10 steered B cells into plasma cells (PC). FDC/HK cells did not direct either pathway, but appeared to provide signals supportive of GC-B cells proliferation in the GC.

To investigate the role of FDC-SM-8D6 in the process of GC-B cell differentiation, mAb 8D6 (50 μg/ml) was added at the beginning of culture of GC-B cells ($1\times10^5$ cell/well) and HK cells ($2\times10^4$ cell/well, 5,000 Rad) in the presence of CD40L (100 ng/ml), IL-2 (30 U/ml), IL-4 (50 U/ml) or IL-10 (50 ng/ml). After 7 days of culture, GC-B cells were harvested for viable cell count by trypan blue exclusive assay. Viable cell recoveries were calculated as a percentage of the initial viable cell number. At the same time, cells were stained with FITC-conjugated anti-CD20 and PE-conjugated anti-CD38 mAbs for FACS analysis. The absolute number of PCs and memory B cells were determined by multiplying viable cell count with $CD20^-CD38^{hi}$ or $CD20^+CD38^{lo}$ cell frequency. The culture supernatant was harvested for measuring the Ig secretion in ELISA.

Figure 7A:
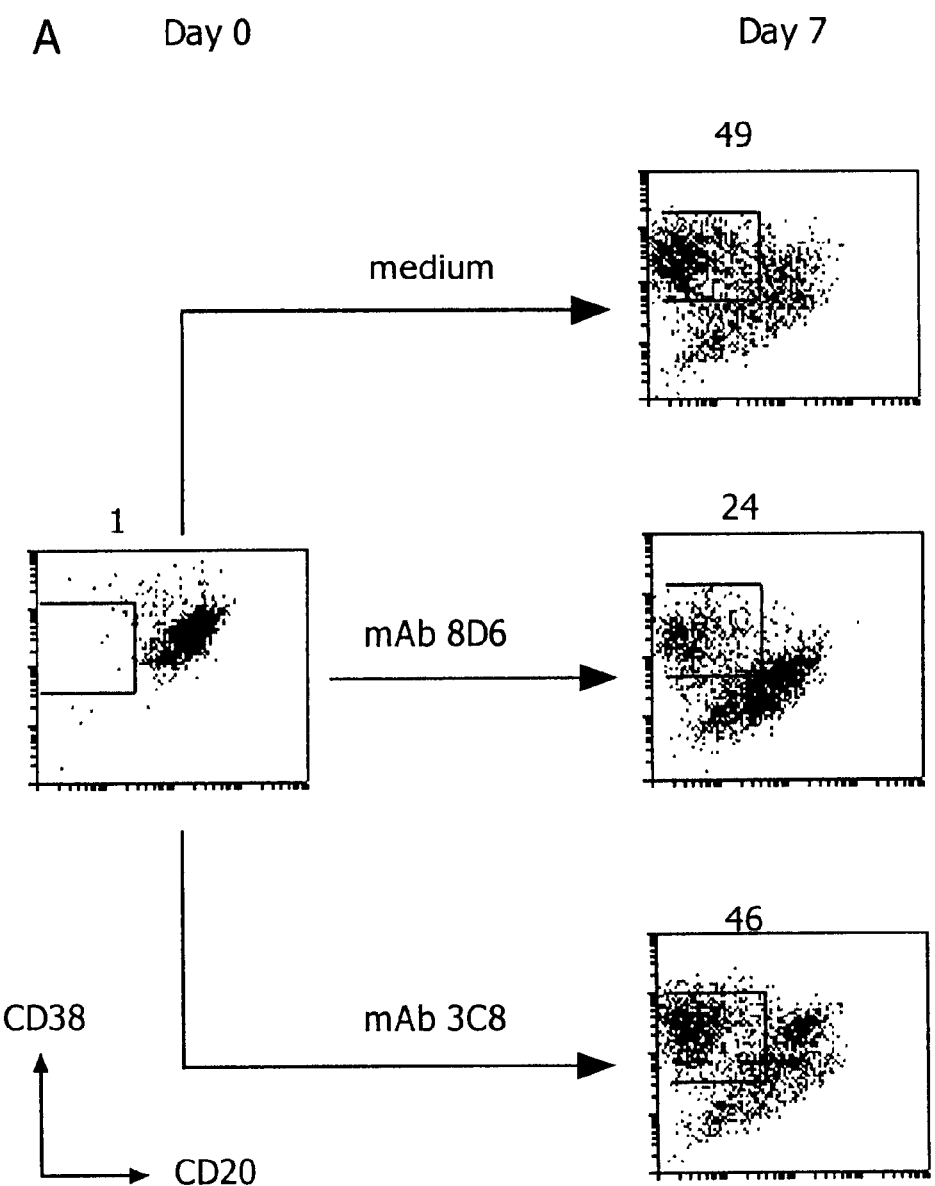

In the culture containing IL-10, viable cell recovery was 920% at the end of culture (FIG. 7B, right). Of total cells recovered, 49% were PC as determined by the number of $CD20^-CD38^{hi}$ cells (FIG. 7A). By day 7, IgG concentration in the supernatant of the culture containing IL-10 was 18.3 µg/ml (FIG. 7D). Compared to the control cultures, the addition of mAb 8D6 reduced the cell recovery from 920% to 435% (FIG. 7B) and the percentage of PC from 49% to 24% (FIG. 7A). The absolute number of PC was decreased by 78% when mAb 8D6 was present (FIG. 7C). The decrease of PC number was also reflected by 61% reduction of IgG secretion if mAb 8D6 was added (FIG. 7D). Such inhibitory effect was not observed in the culture containing isotype matched control mAb 3C8 which bound FDC, but which did not inhibit the FDC/HK cell-mediated GC-B cell growth. However, mAb 8D6 did not affect memory B cell proliferation in the culture containing IL-4 (FIGS. 7B–7D, left). These data indicate that mAb 8D6 selectively inhibited PC generation and reduced IgG secretion in the cultures containing IL-10.

The inhibitory effect of mAb 8D6 was observed only when mAb 8D6 was added at the beginning of the cultures. When mAb 8D6 was added 3 days after initiation of the culture, there was no significant inhibitory effect (FIGS. 7B–D, gray bars). These results indicate that the stimulation by FDC-SM-8D6 in the early stage of PC generation is critical.

Figure 8:
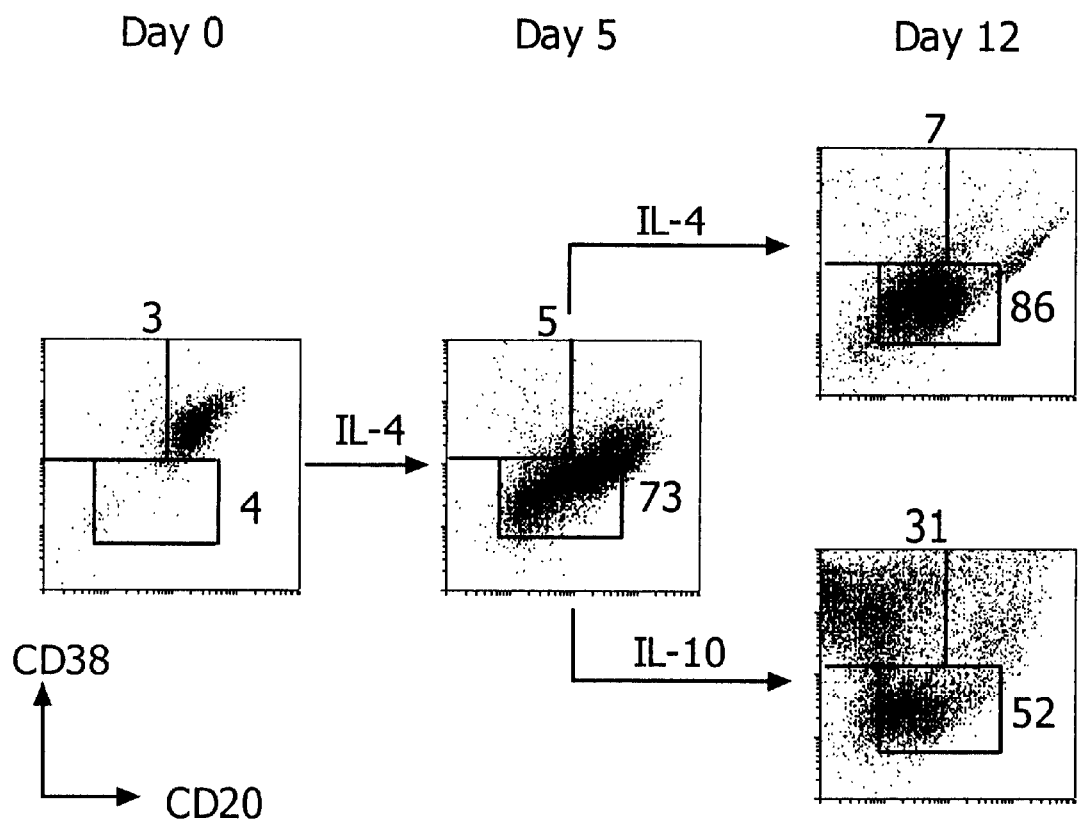
FIG. 8 depicts the differentiation of centrocytes into plasma cells (PC) in the presence of IL-10. Centrocytes were generated by culturing GC-B cells for 5 days in the presence of HK cells, CD40L, IL-2 and IL-4. The cells were washed and re-cultured with IL-4 or IL-10 for 7 additional days in the presence of HK cells, CD40L, and IL-2. At the end of culture, the harvested cells were stained with anti-CD20 and anti-CD38 mAbs for FACS analysis. Percentages of PCs ($CD20^-CD38^{hi}$) or memory B cells ($CD20^+CD38^{lo}$) are indicated by the numbers adjacent to their gates.
Figure 9:
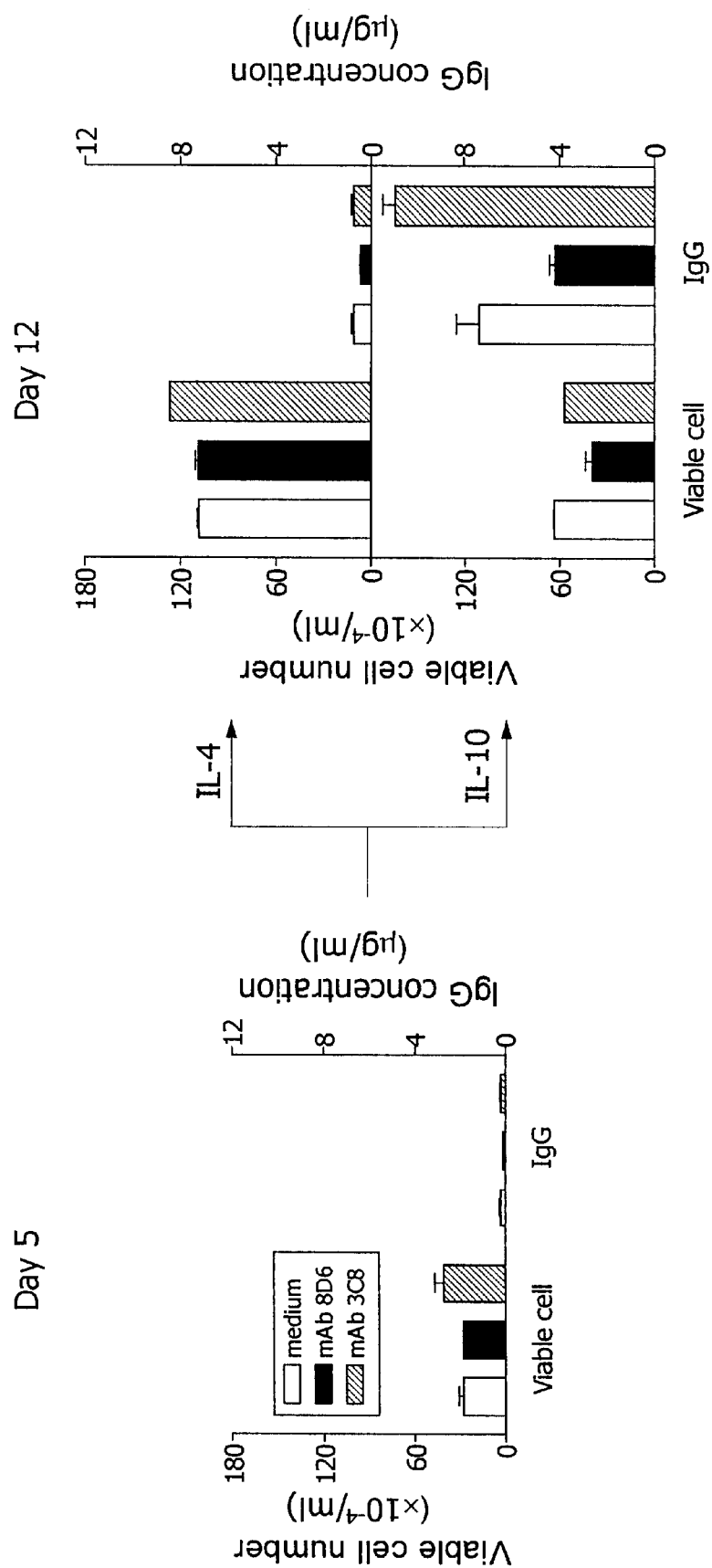
FIG. 9 depicts the inhibition by mAb 8D6 of PC generation from centrocytes in culture with IL-10. GC-B cells were cultured in two steps as described in Example 7. Viable cell number and IgG secretion assessed at the end of both culture steps without mAb (open), with mAb 8D6 (black) or control mAb 3C8 (hatched) are shown.

The specific function of FDC-SM-8D6 in the generation of PCs was further investigated. Centrocytes were generated by culturing centroblasts for 5 days in the presence of HK cells, CD40L, IL-2, and IL-4 in the first step of culture. In the second step of culture, IL-4 was replaced by IL-10, and cells were cultured for an additional 7 days. At the end of the 7-day culture, 31% of recovered cells were determined to be $CD20^-CD38^{hi}$ PC (FIG. 8). In the same experiment, 7.4 µg/ml of IgG was detected in the culture supernatant (FIG. 9). Meanwhile, the culture containing IL-4 did not produce PC or IgG. The addition of mAb 8D6 reduced viable cell number by 38% in the second step culture containing IL-10, whereas it did not affect cell growth in the culture containing IL-4 throughout. The selective inhibition of PC generation by mAb 8D6 was confirmed by 43% reduction of IgG secretion in the culture with IL-10, but not in the culture with IL-4. These results indicate that the target cells of FDC-SM-8D6 are PC precursors in the GC.

What is claimed is:

1. Monoclonal antibody 8D6, wherein said monoclonal antibody has an ATCC deposit number designated as PTA-3231.

2. A composition comprising the monoclonal antibody of claim 1 and a pharmaceutically acceptable carrier.

3. A functional derivative of mAb 8D6, wherein said mAb 8D6 has an ATCC deposit number designated as PTA-3231, and wherein said functional derivative retains the antigenic specificity of mAb 8D6 and suppresses B cell growth or differentiation.

4. The functional derivative of mAb 8D6 of claim 3, wherein said functional derivative is selected from the group consisting of Fab, Fab', F(ab')$_2$, a single chain antibody, and a chimeric antibody.

5. A composition comprising the functional derivative of claim 3 and a pharmaceutically acceptable carrier.

6. The composition of claim 5, wherein said functional derivative is selected from the group consisting of a Fab fragment, a Fab' fragment, a F(ab')$_2$ fragment, a single chain antibody, and a chimeric antibody.

7. A hybridoma cell line, having the ATCC deposit number designated as PTA-3231.

* * * * *